US012691297B2

(12) United States Patent　　　　(10) Patent No.:　US 12,691,297 B2

Choi et al.　　　　　　　　　　　　(45) Date of Patent:　　Jul. 28, 2026

(54) LASER IRRADIATION DEVICE FOR ORAL TREATMENT AND MANUFACTURING METHOD THEREOF

(71) Applicant: P-TECH CO., LTD., Pyeongtaek-si (KR)

(72) Inventors: Yo Sung Choi, Pyeongtaek-si (KR); Jung Eun Kim, Seoul (KR); In Young Jo, Seoul (KR); Hyung Kwon Byeon, Seoul (KR)

(73) Assignee: P-TECH CO., LTD., Pyeongtaek-si (KR)

( * ) Notice: Subject to any disclaimer, the term of this patent is extended or adjusted under 35 U.S.C. 154(b) by 304 days.

(21) Appl. No.: 18/453,468

(22) Filed: Aug. 22, 2023

(65) Prior Publication Data

US 2024/0066314 A1　　Feb. 29, 2024

(30) Foreign Application Priority Data

Aug. 25, 2022　　(KR) ........................ 10-2022-0106601
Nov. 10, 2022　　(KR) ........................ 10-2022-0149751

(51) Int. Cl.
　　*A61N 5/06*　　　　(2006.01)
　　*A61N 5/067*　　　(2006.01)
(52) U.S. Cl.
　　CPC ........... *A61N 5/0603* (2013.01); *A61N 5/067* (2021.08); *A61N 2005/0606* (2013.01);
　　　　　　　　　(Continued)
(58) Field of Classification Search
　　CPC .................. A61N 5/0603; A61N 5/067; A61N 2005/0606; A61N 2005/0626;
　　　　　　　　　(Continued)

(56) References Cited

U.S. PATENT DOCUMENTS 7,182,086 B2 *　2/2007　Fujieda ................... C08L 53/00
　　　　　　　　　　　　　　　　　　　　525/333.3
11,376,444 B1 *　7/2022　Kothari ............... A61N 5/0603
　　　　　　　　　　(Continued)

FOREIGN PATENT DOCUMENTS

JP　　　　2010131181 A　*　6/2010
JP　　　2020-525205 A　　8/2020
　　　　　　　　　(Continued)

OTHER PUBLICATIONS

Translation of KR 102025614 B1 (Year: 2019).*
　　　　　　　　　(Continued)

*Primary Examiner* — Michael W Kahelin
*Assistant Examiner* — Attiya Sayyada Hussaini
(74) *Attorney, Agent, or Firm* — You & IP, LLC

(57) ABSTRACT

A method of manufacturing a laser irradiation device for oral treatment includes (a) molding a base frame having a tongue fixing frame part convexly formed upward so that the tongue is inserted into a lower space thereof and a teeth seating part concavely formed so that human teeth are seated therein, (b) assembling an LED strip with respect to the base frame, the LED strip having a plurality of laser diodes installed on a flexible circuit board to correspond to the shape of the base frame, (c) injecting a liquid light-transparent resin material into an upper light-transparent cover and a lower light-transparent cover respectively corresponding to the shapes of upper and lower parts of the base frame, and (d) respectively pressing the upper light-transparent cover and the lower light-transparent cover vertically upward and downward with respect to the base frame.

6 Claims, 10 Drawing Sheets

(52) U.S. Cl.
CPC ................. *A61N 2005/0626* (2013.01); *A61N*
*2005/0652* (2013.01); *A61N 2005/0659*
(2013.01); *A61N 2005/0663* (2013.01)

(58) Field of Classification Search
CPC .... A61N 2005/0652; A61N 2005/0659; A61N
2005/0663
See application file for complete search history.

(56) References Cited

U.S. PATENT DOCUMENTS

| | | | | |
|---|---|---|---|---|
| 11,865,356 | B1 * | 1/2024 | Vorwaller | ............ A61N 5/0613 |
| 2020/0101311 | A1 * | 4/2020 | Tahghighi Jafarzadeh | ................. A61N 5/0613 |
| 2021/0267738 | A1 * | 9/2021 | Mackie | .................. A61C 19/06 |
| 2022/0054226 | A1 * | 2/2022 | Gregg, II | ............. A61C 19/004 |

FOREIGN PATENT DOCUMENTS

| | | | | | |
|---|---|---|---|---|---|
| KR | 10-2013-0057692 | A | | 6/2013 | |
| KR | 10-1554721 | B1 | | 9/2015 | |
| KR | 102025614 | B1 | * | 9/2019 | ........... A61N 5/0603 |
| KR | 20200027407 | A | * | 3/2020 | ........... A61N 5/0603 |
| KR | 10-2021-0030086 | A | | 3/2021 | |
| KR | 10-2022-0078877 | A | | 6/2022 | |
| WO | 2018-140560 | A1 | | 8/2018 | |
| WO | 2021069805 | A1 | | 4/2021 | |

OTHER PUBLICATIONS

Translation of KR 20200027407 A (Year: 2020).*
Translation of JP 2010131181 A (Year: 2010).*
Korean Office Action mailed on Jul. 15, 2024.

* cited by examiner

250

210

INJECT
LIQUID
SILICONE

INJECT
LIQUID
SILICONE

230

LASER IRRADIATION DEVICE FOR ORAL TREATMENT AND MANUFACTURING METHOD THEREOF

BACKGROUND

Technical Field

The present disclosure relates to a laser irradiation device used for oral treatment and having a novel mouthpiece structure for facilitating laser treatment on an area vulnerable to oral mucositis in the oral cavity, and a manufacturing method thereof.

Related Art

In general, low-level laser therapy (LLLT) is a therapy method that promotes a spontaneous therapy effect on a damaged body part by a photobiological control mechanism that uses laser light to control bioactivity. The LLLT technique is used in various fields such as skin and beauty, ophthalmology, dentistry, pain relief, wound healing, neurology, oncology, etc. In particular, in dentistry, a laser irradiation device is used for treatment of tooth whitening, oral pain relief, oral mucositis, etc.

On the other hand, there are frequent cases in which patients with moderate or higher oral mucositis occur after chemotherapy or radiotherapy. Recently, it has been reported in many papers that as a result of an experiment with low-level laser therapy on animal models that induced oral mucositis, anti-inflammatory effects such as wound healing, collagen synthesis, and neutropenia were shown.

Korean Patent Publication No. 10-2013-0057692 entitled "Mouthpiece for Oral Treatment and Oral Treatment Device having the Same" and Korean Patent No. 10-1554721 entitled "Light Irradiation Device for Oral Cavity" propose a treatment device that uniformly irradiates a laser beam toward the inside of the oral cavity while the patient bites the mouthpiece. However, the above documents' related art is provided such that the treatment devices are configured to spread the laser beam into the oral cavity using a beam expander or transmit the laser beam into the oral cavity in a light-reflective manner using a reflection unit, causing problems in that the intensity of the laser light is weak and laser energy is weakened in the process of reaching inflamed part, making it difficult to cause damage to the living body.

Commonly, regions where oral mucositis frequently occurs after chemotherapy are vulnerable regions located deep in the oral cavity, such as the oral vestibule, periodontium, sublingual gland, tonsils, etc. However, the above related art has a limit in treatment of oral mucositis due to structural problems in which the amount of light is concentrated on the front side of the oral cavity and it is thus difficult for the light to reach vulnerable regions with high intensity. In addition, the above related art has another problem in that light is irradiated at a single wavelength so that light cannot be transmitted deeply to a desired part as energy is lost in the process of penetrating into the living body.

In addition, in the laser irradiation device for oral treatment, the most important point is that the laser light should be directly irradiated to the oral mucositis region of a patient and the loss in the light path should be small.

SUMMARY

Various embodiments of the present disclosure are directed to a laser irradiation device for oral treatment which enables laser light to be irradiated to deep regions in the oral cavity by using a mouthpiece customized for an oral structure considering teeth and a tongue, enable laser treatment in close proximity to a vulnerable region in the oral cavity, such as the oral vestibule, periodontium, sublingual gland, tonsil, etc., by using a base frame and an LED strip, and provides high light transmittance, and a manufacturing method thereof.

The object of the present invention is not limited to the objects mentioned above, and other objectives not mentioned will be clearly understood by those skilled in the art from the following description.

In an embodiment of the present disclosure, a method of manufacturing a laser irradiation device for oral treatment includes: (a) molding a base frame having a tongue fixing frame part convexly formed upward so that the tongue is inserted into a lower space thereof and a teeth seating part concavely formed so that human teeth are seated therein; (b) assembling an LED strip with respect to the base frame, the LED strip having a plurality of laser diodes installed on a flexible circuit board to correspond to the shape of the base frame; (c) injecting a liquid light-transparent resin material into an upper light-transparent cover and a lower light-transparent cover respectively corresponding to the shapes of upper and lower parts of the base frame; and (d) respectively pressing the upper light-transparent cover and the lower light-transparent cover vertically upward and downward with respect to the base frame.

In an aspect of the present disclosure, in the step (a), the base frame is molded to form, on the tongue fixing frame part, a plurality of palate-irradiation seating grooves concavely formed such that the laser diodes are seated therein in a position facing upwards, and a tongue-irradiation cutout cut out such that the laser diodes are mounted thereon in a position facing downwards.

In an aspect of the present disclosure, in the step (a), the base frame is molded such that an end of the tongue fixing frame part is bent at an obtuse angle to form an arc-shaped bent surface for irradiation of the tonsil.

In an aspect of the present disclosure, in the step (a), upper and lower surfaces of a wall portion standing around the teeth seating part are respectively provided with first seating grooves for irradiation of the oral vestibule, which are formed concavely to have mounting surfaces bent at a first angle toward the oral vestibule located on the molar side of the human body.

In an aspect of the present disclosure, in the step (a), the upper and lower surfaces of the wall portion are respectively provided with second seating grooves for irradiation of the oral vestibule, which are formed concavely to have mounting surfaces bent at a second angle smaller than the first angle toward the oral vestibule located on the canine side of the human body.

In an aspect of the present disclosure, in the step (a), the upper and lower surfaces of the wall portion are respectively provided with third seating grooves for irradiation of the oral vestibule, which are formed concavely to have mounting surfaces bent at a third angle smaller than the second angle toward the oral vestibule located on the front-teeth side of the human body.

In an aspect of the present disclosure, each of the laser diodes is a three-wavelength laser diode in which a first laser diode having a wavelength of 650 nm to 690 nm, a second laser diode having a wavelength of 810 nm to 850 nm, and a third laser diode having a wavelength of 890 nm to 930 nm are configured in the form of a single chip.

In an aspect of the present disclosure, the upper light-transparent cover and the lower light-transparent cover are provided with a plurality of discharge holes through which the liquid light-transparent resin material is discharged to the outside, the method further comprising: after the step (d), (e) removing the liquid light-transparent resin material overflowing to the outside through the discharge holes.

In an aspect of the present disclosure, the discharge holes are located at a position off an optical axis of the laser diode.

In an aspect of the present disclosure, the method further comprises: after step (e), (f) curing the liquid light-transparent resin material accommodated in the upper light-transparent cover and the lower light-transparent cover.

In another embodiment of the present disclosure, a laser irradiation device for oral treatment includes: a base frame having a tongue fixing frame part convexly formed upward so that the tongue is inserted into a lower space thereof and a teeth seating part concavely formed so that human teeth are seated therein; an LED strip having a plurality of laser diodes installed on a flexible circuit board to correspond to the shape of the base frame; a light-transparent cover coupled to the outside of the base frame and through which laser light emitted from the laser diodes is transmitted; a cable connected to one end of the LED strip to supply operation power to the laser diodes; and a main body including a power supply configured to supply the operation power and a controller configured to control the operation of the laser diodes.

In an aspect of the present disclosure, the light-transparent cover comprises an upper light-transparent cover and a lower light-transparent cover corresponding to the shape of upper and lower portions of the base frame and having a plurality of discharge holes through which the liquid light-transparent resin material injected into the upper and lower light-transparent covers is discharged to the outside during the pressing process.

In an aspect of the present disclosure, the discharge holes are located at a position off an optical axis of the laser diode.

In an aspect of the present disclosure, the tongue fixing frame part is provided with a plurality of palate-irradiation seating grooves concavely formed such that the laser diodes mounted on one side of the LED strip are seated therein in a position facing upwards, and a tongue-irradiation cutout cut out such that the laser diodes mounted on the other side of the LED strip are mounted thereon in a position facing downwards.

In an aspect of the present disclosure, the base frame is provided such that an end of the tongue fixing frame part is bent at an obtuse angle to form an arc-shaped bent surface for irradiation of the tonsil, and one end of the LED strip is provided with a tonsil division strip branching in an arc shape and on which a plurality of tonsil-irradiation laser diodes is mounted on the bent surface for irradiation of the tonsil.

In an aspect of the present disclosure, the other end of the LED strip is provided with a sublingual gland division strip branching in a horseshoe shape, and a plurality of sublingual gland-irradiation laser diodes is mounted at predetermined intervals on the sublingual gland division strip, the sublingual gland division strip being mounted on the bottom surface of the base frame.

In an aspect of the present disclosure, each of the laser diodes is a three-wavelength laser diode in which a first laser diode having a wavelength of 650 nm to 690 nm, a second laser diode having a wavelength of 810 nm to 850 nm, and a third laser diode having a wavelength of 890 nm to 930 nm are configured in the form of a single chip.

In an aspect of the present disclosure, the controller operates in any one mode, among a pulse output mode for alternatingly outputting pulses of a first laser diode, a second laser diode, and a third laser diode, a first continuous wave output mode for outputting the first laser diode in the form of a continuous wave, a second continuous wave output mode for outputting the second laser diode in the form of a continuous wave, and a third continuous wave output mode for outputting the third laser diode in the form of a continuous wave.

In an aspect of the present disclosure, the controller sets the pulse width of the second laser diode to be three times longer than that of other laser diodes in the pulse output mode.

According to the laser irradiation device for oral treatment and the manufacturing method thereof, laser light can be irradiated to deep regions in the oral cavity by using the mouthpiece customized for an oral structure considering teeth and tongue of a human body, laser treatment can be performed in close proximity to the vulnerable region in the oral cavity, such as the oral vestibule, periodontium, sublingual gland, tonsil, etc., by using the base frame and the LED strip, and light loss in the light path can be minimized and high light transmittance can be secured by injecting a liquid light-transparent resin material between the light-transparent cover and the optical means, so that the laser light causes appropriate bio-damage to the biological tissue in the oral cavity to generate the photobiological control mechanism, thereby providing a very effective advantage in treating oral mucositis.

The effects of the present invention are not limited to those mentioned above, and other problems not mentioned may be clearly understood by those skilled in the art from the following description.

DETAILED DESCRIPTION

Figure 1:
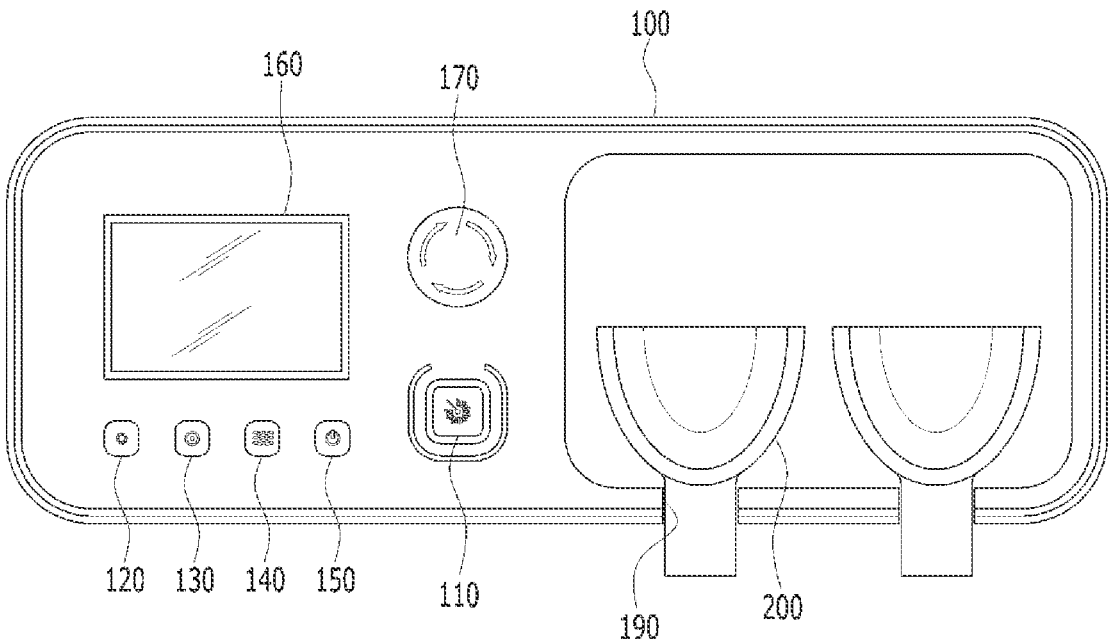
FIG. 1 is a front view illustrating a laser irradiation device for oral treatment according to the present disclosure.

Additional objects, features, and advantages of the present disclosure will be understood more clearly from the following detailed description and the accompanying drawings.

Prior to the detailed description of the present disclosure, the present disclosure may be variously modified and may have various embodiments, and it should be understood that examples to be described below and illustrated in the drawings is not intended to limit the present disclosure to specific embodiments and include all modifications, equivalents, and substitutes included in the spirit and technical range of the present disclosure.

It will be understood that when an element is referred to as being "connected" or "coupled" to another element, it can be directly connected or coupled to the other element or intervening elements may be present therebetween. In contrast, when an element is referred to as being "directly connected" or "directly coupled" to another element, there are no intervening elements therebetween.

The terminology used herein is for the purpose of describing particular embodiments only and is not intended to limit the disclosure. As used herein, the singular forms "a", "an" and "the" include the plural forms as well, unless the context clearly indicates otherwise. It will be further understood that the terms "comprises", "comprising,", "includes" and/or "including", when used herein, specify the presence of stated features, numbers, steps, operations, elements, components, or combinations thereof, but do not preclude the presence or addition of one or more other features, numbers, steps, operations, elements, components, or combinations thereof.

Furthermore, a term such as " . . . section", " . . . unit", and " . . . module" described in this specification means a unit for processing at least one function or operation, and this may be implemented with hardware, software, or a combination of the hardware and the software.

Furthermore, in the following description with reference to the accompanying drawings, the same reference numerals are given to the same components and a redundant description thereof will be omitted. Detailed descriptions related to well-known functions or configurations will be ruled out in order not to unnecessarily obscure subject matters of the present disclosure. Throughout the specification, when a step is "on" or "before" another step, this includes the same right not only when one step is in a direct time series relationship with another, but also when it is in an indirect time series relationship where the order of two steps can be changed, such as a mixing step after each step.

Figure 2:
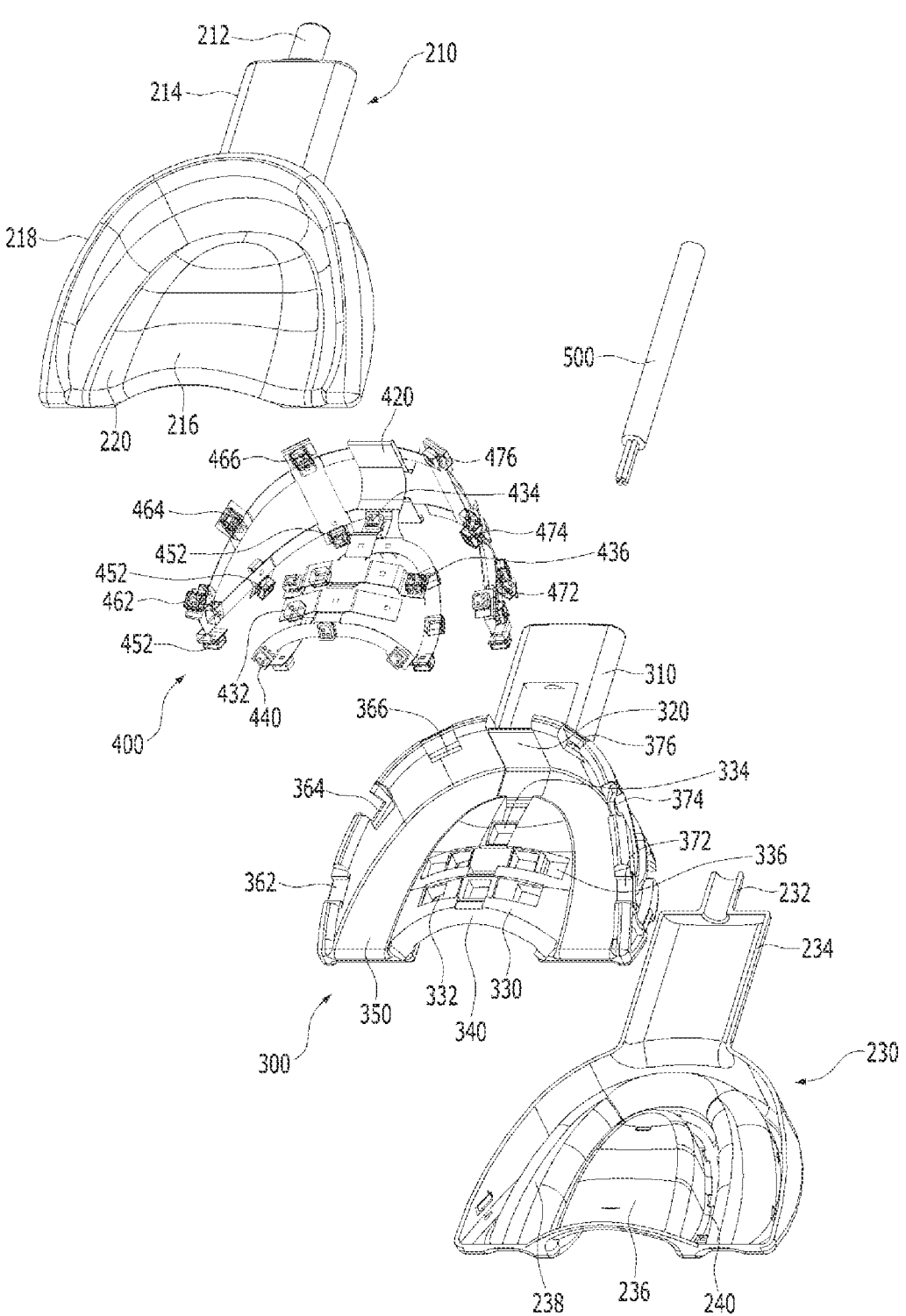
FIG. 2 is an exploded perspective view illustrating a mouthpiece for laser treatment of the oral cavity according to the present disclosure.
Figure 3:
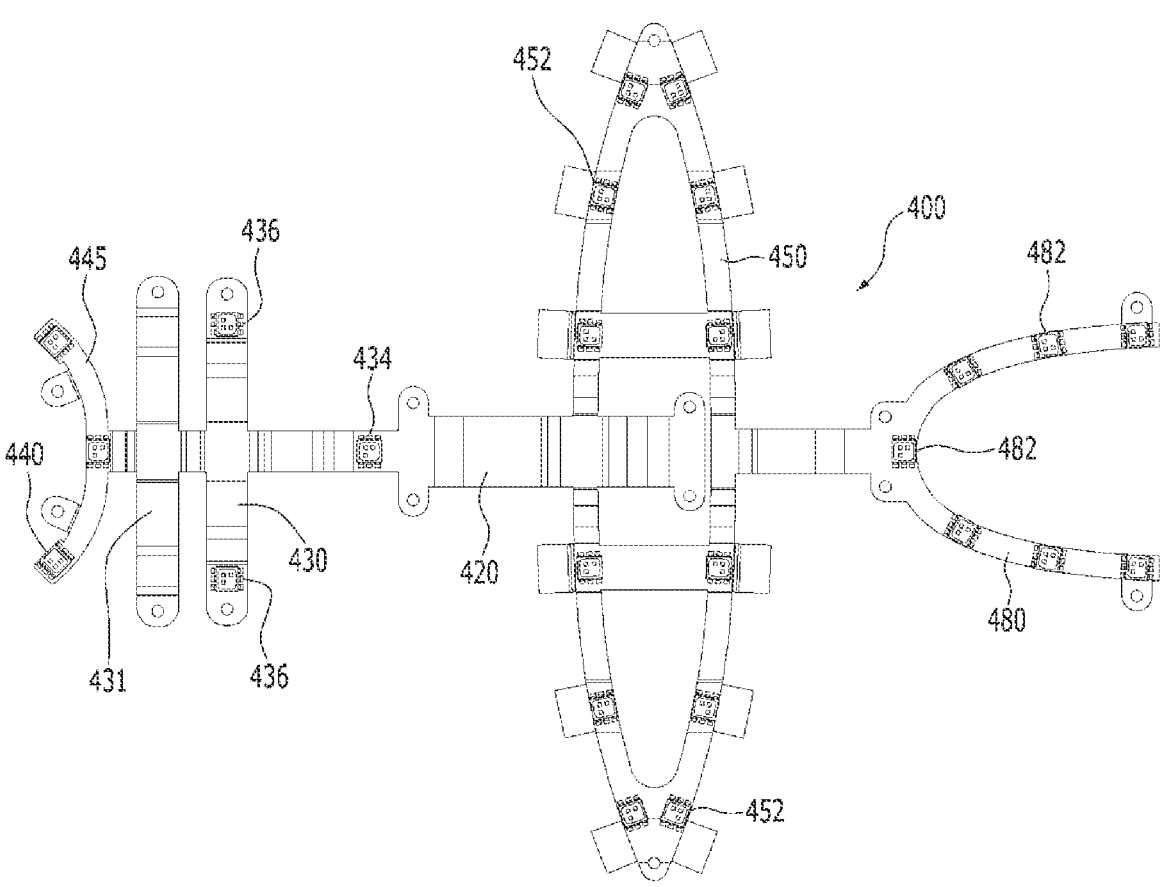
FIG. 3 is a front exploded view illustrating the unfolded state of an LED strip according to the present disclosure.
Figure 4:
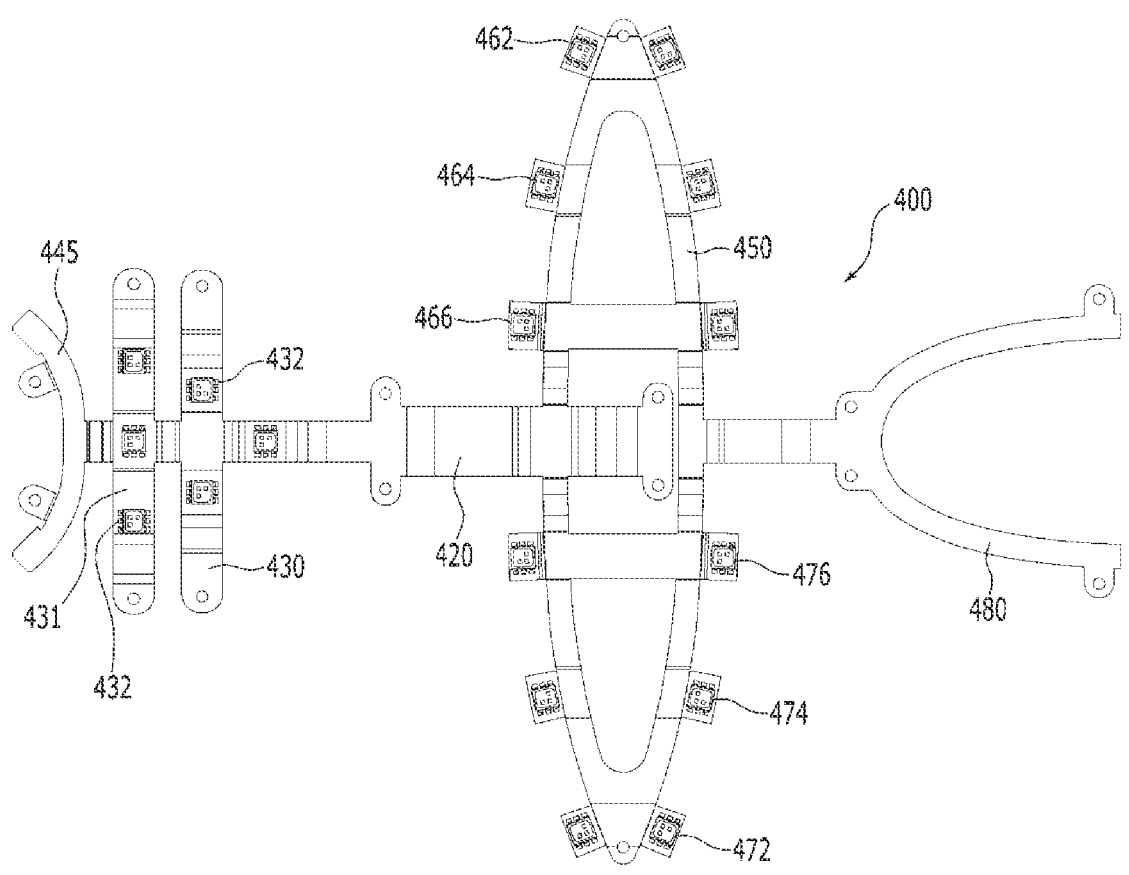
FIG. 4 is a rear exploded view illustrating the unfolded state of the LED strip according to the present disclosure.
Figure 5:
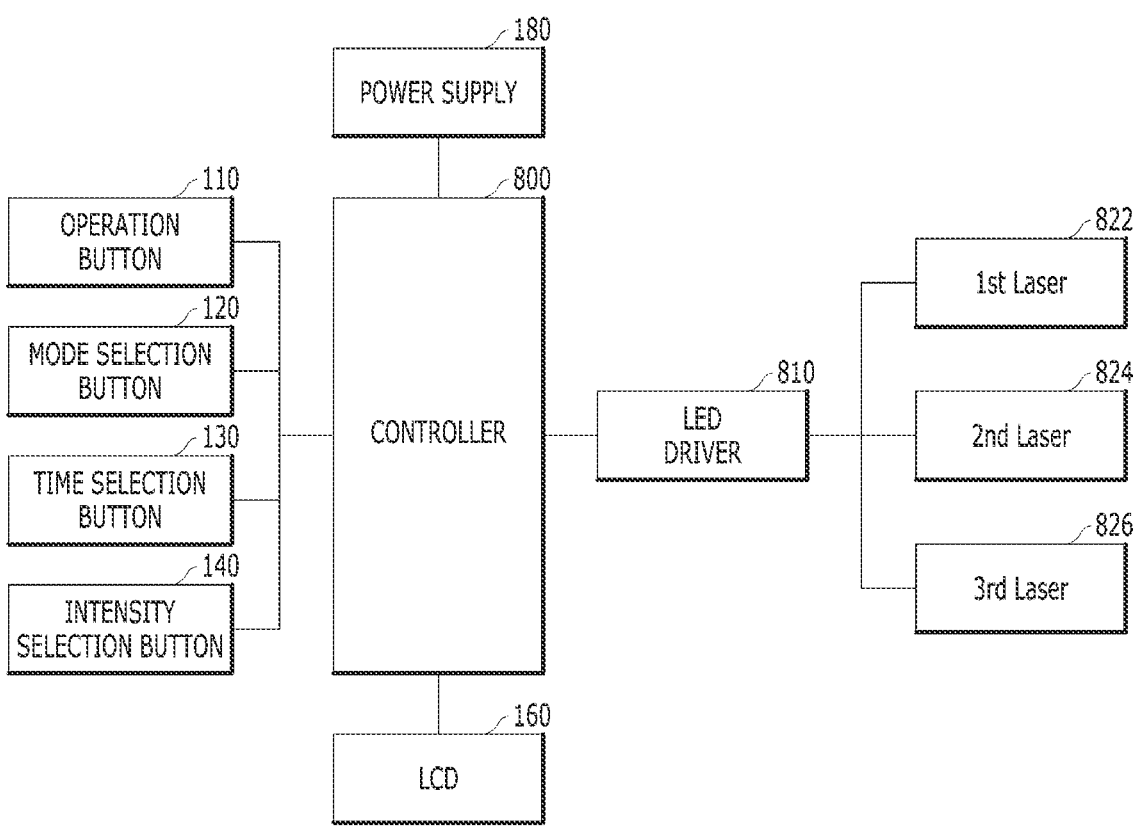
FIG. 5 is a block diagram illustrating a laser irradiation device for oral treatment according to the present disclosure.

FIG. 1 is a front view illustrating a laser irradiation device for oral treatment according to the present disclosure, FIG. 2 is an exploded perspective view illustrating a mouthpiece for laser treatment of the oral cavity according to the present disclosure, FIG. 3 is a front exploded view illustrating the unfolded state of an LED strip according to the present disclosure, FIG. 4 is a rear exploded view illustrating the unfolded state of the LED strip according to the present disclosure, and FIG. 5 is a block diagram illustrating a laser irradiation device for oral treatment according to the present disclosure. The configuration of the laser irradiation device for oral treatment according to the present disclosure will be first described with respect to FIGS. 1 to 5, and then a method of manufacturing the laser irradiation device for oral treatment according to the present disclosure will be described.

Referring to FIGS. 1 to 5, the laser irradiation device for oral treatment according to the present disclosure includes a main body 100, a cable 500, and a mouthpiece 200.

Referring to FIGS. 1 and 5, the main body 100 houses a power supply 180 and a controller 800. For example, the power supply 180 may be a battery. The battery may be a battery mountable in the main body 100 or a rechargeable secondary battery. As another example, the power supply 180 may include a converter that converts applied commercial AC power into DC power. Although not shown, a battery compartment, a charging port for connecting a charger for charging a secondary battery, or a connection jack for connecting to an adapter connected to a commercial AC power source are installed on the rear surface of the main body 100. The controller 800 outputs an operation signal to an LED driver 810, which drives laser diodes in a pulse mode or a continuous wave mode to irradiate the inflamed regions in the oral cavity.

The laser diodes described below may be a three-wavelength laser diode in which a first laser diode 822 having a wavelength of 650 nm to 690 nm, a second laser diode 824 having a wavelength of 810 nm to 850 nm, and a third laser diode having a wavelength of 890 nm to 930 nm are configured in the form of a single chip. Preferably, the first laser diode 822 may have a wavelength of 670 nm, the second laser diode 824 may have a wavelength of 830 nm, and the third laser diode 826 may have a wavelength of 910 nm.

Referring to FIG. 1, the main body 100 includes an operation button 110, a mode selection button 120, a time selection button 130, an intensity selection button 140, a power button 150, a display 160, and an emergency stop button 170 on the front surface thereof.

The operation button 110 is a button for turning on/off irradiation of laser light. The mode selection button 120 is a button for selecting a laser light irradiation mode. The laser light irradiation mode has four modes of a pulse output mode, a first continuous wave mode, a second continuous wave mode, and a third continuous wave mode, which are sequentially selected whenever the mode selection button 120 is input once.

The time selection button 130 is a button for selecting a laser light irradiation time. For example, the operation time increases by 10 minutes each time the button is pressed once, and when the time selection button 130 is pressed again after selecting the 60-minute operation, the operation mode is changed to 10-minute operation mode. The intensity selection button 140 is a button that adjusts the laser output intensity of the selected operation mode step by step.

The power button 150 is a button that selects turning on or off the power of the entire device. The display 160 is a unit that displays the currently selected laser operation mode, operation time, and output intensity to the user. The emergency stop button 170 is a button for immediately stopping the operation of the device and cutting off power in case of an emergency.

Referring to FIG. 1, one area of the front side of the main body 100 is provided with a holding space that is recessed so that several mouthpieces 200d can be held therein, and a hook grooves 190 in which the mouthpieces 200 can be fixedly hooked. The cable 500 connects the main body 100 and the mouthpiece 200 to supply operation power of the main body 100 to respective laser diodes installed in the mouthpiece 200.

Referring to FIG. 2, the mouthpiece 200 includes an assembly of a base frame 300, an LED strip 400, and light-transparent covers 210 and 230.

The base frame 300 includes seating grooves 334, 336, 362, 364, 366, 372, 374, 376 and a cutout 332 in which a plurality of laser diodes is seated, and a tongue fixing flame part 330 that is convexly formed upward so that the tongue is inserted into a lower space thereof, and a teeth seating part 350 in which upper and lower teeth are seated.

The LED strip 400 is in the form of a strip in which a plurality of laser diodes installed by being inserted into the seating grooves 334, 336, 362, 364, 366, 372, 374, 376 and the cutout 332 are mounted on a flexible circuit board.

A connector 310 formed at an end of the base frame 300 is a portion into which an end of the cable 500 is inserted, and the wires of the cable 500 are connected to the LED strip 400 within the connector 310. The LED strip 400 is formed with a double-sided flexible circuit board, and the strips of the flexible circuit board and the laser diodes installed on the flexible circuit board are fitted into grooves and holes formed in the base frame 300 to fix the position of the LED strip 400.

Referring to FIGS. 3 and 4, the LED strip 400 has a structure in which a plurality of division strips branch and extend from a central thick film part, and a plurality of laser diodes are mounted on respective branching strips. The LED strip 400 is formed with a double-sided flexible circuit board, and as illustrated in FIGS. 3 and 4, a plurality of laser diodes is mounted on the front and rear surfaces thereof, respectively, so that even through the tongue fixing frame 330 of the base frame 300 is made into a single frame, it is possible for the LED strip to irradiate laser light to the palate and the flat of the tongue.

A strip seating groove 320 is formed adjacent to the connector 310 of the base frame 300. In addition, a central support portion 420 of the LED strip 400 is folded and fitted into the strip seating groove 320.

Referring to FIG. 3, the LED strip 400 has an arc-shaped tonsil division strip 445 formed at one end thereof and a horseshoe-shaped sublingual gland division strip 480 formed at the other end with respect to the central support portion 420. Tonsil-irradiation laser diodes 440 are mounted at predetermined intervals on the tonsil division strip 445 to irradiate laser light to the tonsil region of the human body. Sublingual gland-irradiation laser diodes 482 are mounted at predetermined intervals on the sublingual gland division strip 480 to irradiate laser light to the sublingual gland region of the human body.

A first transverse strip 430 and a second transverse strip 431 are transversely formed between the central support portion 420 and the tonsil division strip 445. In the first transverse strip 430, a laser diode 436 is mounted to irradiate laser light to the lateral side of the palate of the human body. A laser diode 434 is mounted between the first transverse strip 430 and the central support portion 420 to irradiate laser light toward the front side of the palate of the human body.

A two-row periodontal division strip 450 whose both ends meet is formed between the central support portion 420 and the sublingual division strip 480. A plurality of laser diodes 452 is mounted on the periodontal division strip 450 to irradiate laser light to the periodontal region of the human body.

Referring to FIG. 4, laser diodes 462, 464, 466, 472, 474, and 476 for irradiating laser light to the oral vestibule of the human body are mounted on a strip protruding outward from the periodontal division strip 450. In addition, six laser diodes 432 for irradiating laser light to the tongue of the human body are mounted adjacent to the first transverse strip 430, the second transverse strip 431, and the central support portion 420.

A process of assembling and mounting the laser diodes described with reference to FIGS. 3 and 4 on the base frame 300 will be described as follows.

On the tongue fixing frame part 330 of the base frame 300, the seating groove 334 for forward irradiation of the palate and the seating groove 336 for lateral irradiation of the palate are formed concavely, and the cutout 332 for tongue-irradiation is cut and formed. The frontal palate-irradiation laser diode 434 of the LED strip 400 is fitted into and coupled to the seating groove 334 in a position facing upwards. The lateral palate-irradiation laser diode 436 of the LED strip 400 is fitted into and coupled to the seating groove 336 in a position facing upwards. The tongue-irradiation laser diode 432 of the LED strip 400 is mounted in the cutout 332 for tongue irradiation in a position facing downwards. That is, in the mouthpiece structure of the present disclosure, even though the tongue fixing frame part 330 is configured as a single frame, the upper-side palate and the lower-side tongue's flat can be simultaneously closely irradiated and treated with laser light by using the double-sided flexible circuit board.

Referring to FIG. 2, the end of the tongue fixing frame part 330 of the base frame 300 is bent at an obtuse angle toward the tonsils in the oral cavity to form a bent surface 340 for tonsil irradiation. Then, the tonsil division strip 445 of the LED strip 400 is seated and assembled onto the bent surface 340 for tonsil irradiation. Therefore, the laser diode 440 for irradiating tonsils can irradiate laser light in close proximity to the tonsil of the human body.

Although not depicted in FIG. 2, a seating portion on which the sublingual division strip 480 is seated is formed at the bottom of the base frame 300. As the sublingual division strip 480 is seated and assembled here, the sublingual irradiation laser diode 482 can irradiate laser light in close proximity to the sublingual gland.

In addition, although not depicted in FIG. 2, on the outer periphery of the base frame 300 (that is, the surface opposite to the surface facing the teeth seating part 350), a plurality of seating grooves for periodontal irradiation is formed in two rows (upper and low periodontal rows). Then, the periodontal division strip 450 of the above-described LED strip 400 is assembled onto the seating groove for periodontal irradiation. Therefore, the laser diode 452 for periodontal irradiation can irradiate laser light in close proximity to the periodontium of the human body.

Referring to FIG. 2, the upper and lower surfaces of the wall portion standing around the teeth seating part 350 of the base frame 300 are provided with first left/right seating grooves 362 and 372 for oral vestibular irradiation, which are formed concavely to have mounting surfaces bent at a first angle toward the oral vestibule located on the upper and lower molar sides of the human body. The first angle is, for example, 90 degrees relative to the vertical wall. The first left seating groove 362 for oral vestibular irradiation and the first right seating groove 372 for oral vestibular irradiation are provided to be symmetrical with respect to the central line of the mouthpiece 200 in the longitudinal direction. In addition, a laser diode 462 for oral vestibular irradiation of the LED strip 400 is mounted in the first left seating groove 362 for oral vestibular irradiation, and a laser diode 472 for oral vestibular irradiation is mounted in the first right seating groove 372 for oral vestibular irradiation.

The upper and lower surfaces of the wall portion are provided with second left/right seating grooves 364 and 374 for oral vestibular irradiation, which are formed concavely to have mounting surfaces bent at a second angle smaller than the first angle toward the oral vestibule located on the upper and lower canine sides of the human body. The second angle is, for example, 60 degrees relative to the vertical wall. The second left seating groove 364 for oral vestibular irradiation and the second right seating groove 374 for oral vestibular irradiation are provided to be symmetrical with respect to the central line of the mouthpiece 200 in the longitudinal direction. In addition, a laser diode 464 for oral vestibular irradiation is mounted in the second left seating groove 364 for oral vestibular irradiation, and a laser diode 474 for oral vestibular irradiation is mounted in the second right seating groove 374 for oral vestibular irradiation.

The upper and lower surfaces of the wall portion are provided with third left/right seating grooves 366 and 376 for oral vestibular irradiation, which are formed concavely to have mounting surfaces bent at a third angle smaller than the second angle toward the oral vestibule located on the upper and lower front-teeth sides of the human body. The third angle is, for example, 30 degrees relative to the vertical wall. The third left seating groove 366 for oral vestibular irradiation and the third right seating groove 376 for oral vestibular irradiation are provided to be symmetrical with respect to the central line of the mouthpiece 200 in the longitudinal direction. In addition, a laser diode 466 for oral vestibular irradiation is mounted in the third left seating groove 366 for oral vestibular irradiation, and a laser diode 476 for oral vestibular irradiation is mounted in the third right seating groove 376 for oral vestibular irradiation.

As described above, since the seating grooves 362 and 372 for irradiation of oral vestibule on the molar side, the seating grooves 364 and 374 for irradiation of oral vestibule on the canine side, and the seating grooves 366 and 376 for irradiation of oral vestibule on the front-teeth side have mounting surfaces at different angles, it is possible to irradiate direct light in very close proximity to the oral mucositis caused in the oral vestibule according to the oral structure.

Referring to FIG. 2, the light-transparent covers 210 and 230 are coupled to the outside of the LED strip 400 so that laser light emitted from the laser diodes is transmitted therethrough. The light-transparent covers 210 and 230 have a structure in which an upper light-transparent cover 210 coupled to the upper side of the LED strip 400 and a lower light-transparent cover 230 coupled to the bottom side of the LED strip come into contact with each other and are assembled.

The upper light-transparent cover 210 and the lower light-transparent cover 230 are made of a silicone material. As will be described later with reference to FIG. 7 or more, a liquid light-transparent resin material is injected into the upper light-transparent cover 210 and the lower light-transparent cover 230 and then cured. The liquid light-transparent resin material is liquid silicone that has substantially the same light transmittance as that of the light-transparent covers 210 and 230 after cured. In this way, by injecting and curing liquid silicone between the upper light-transparent cover 210 and the lower light-transparent cover 230, the LED strip 400 can be firmly fixed to the base frame 300, and laser light can be irradiated to the affected area with high transmittance. Preferably, by forming a plurality of discharge holes in the upper light-transparent cover 210 and the lower light-transparent cover 230 so that during the process of pressing the light-transparent covers 210 and 230 with respect to the base frame 300, the liquid silicone flows to the outside through the discharge holes, thereby solving the problem of deterioration in light transmittance caused by bubbles being generated inside the light-transparent covers 210 and 230.

The upper light-transparent cover 210 has a cable insertion hole 212 into which the cable 500 is inserted at the end of the connector 214 protruding out of the lips when the user bites the mouthpiece 200 with his teeth. The connector 214 has a length that can extend a sufficient length outside the lips when a patient bites the mouthpiece 200. A tongue fixing convex portion 216 is formed convexly upward to correspond to the upper surface of the tongue fixing frame part 330 of the base frame 300. A U-shaped upper oral vestibular insertion portion 218 protrudes upward from the upper light-transparent cover 210 and is inserted into the upper oral vestibular space between the upper teeth and the upper lip. An upper teeth seating portion 220 recessed inward along the upper oral vestibular insertion portion 218 is a portion where the ends of the upper teeth are seated. The mouthpiece 200 is stably supported in the upper part of the oral cavity of the patient by the upper oral vestibular insertion portion 218 and the upper teeth seating portion 220.

The lower light-transparent cover 230 has a cable insertion hole 232 into which the cable 500 is inserted at the end of the connector 234. A tongue fixing convex portion 236 is formed convexly upward to correspond to the lower surface of the tongue fixing frame part 330 of the base frame 300, and the upper portion of the tongue of the human body is supported on the undersurface of the tongue fixing convex portion 236 to fix the position of the tongue during treatment. A U-shaped lower oral vestibular insertion portion 238 protrudes downward from the lower light-transparent cover 230 and is inserted into the lower oral vestibular space between the lower teeth and the lower lip. A lower teeth seating portion 240 recessed inward along the lower oral vestibular insertion portion 238 is a portion where the ends of the lower teeth are seated. The mouthpiece 200 is stably supported in the lower part of the oral cavity of the patient by the lower oral vestibular insertion portion 238 and the lower teeth seating portion 240.

Figure 6:
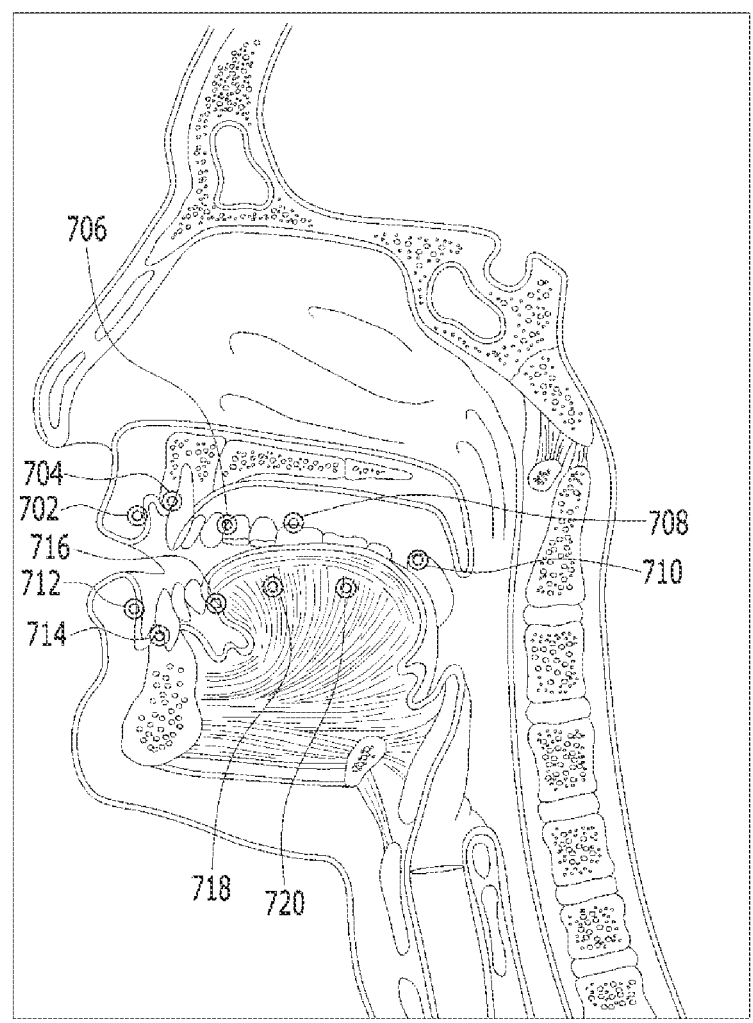
FIG. 6 is a view illustrating regions vulnerable to oral mucositis that can be simultaneously laser-treated by using the mouthpiece according to the present disclosure.

FIG. 6 is a view illustrating regions vulnerable to oral mucositis that can be simultaneously laser-treated by using the mouthpiece according to the present disclosure.

As in the oral cross-sectional view of FIG. 6, the regions where oral mucositis frequently occurs are the upper vestibule 702, upper incisor periodontal portion 704, upper canine periodontal portion 706, upper molar periodontal portion 708, tonsil 710, lower oral vestibule 712, lower incisor periodontal portion 714, lower canine periodontal portion 716, lower molar periodontal portion 718, and sublingual gland 720. In addition, these regions correspond to vulnerable regions that are not well treated by conventional laser irradiation devices for oral treatment.

Since the laser irradiation device for oral treatment according to the present disclosure has the mouthpiece 200 having above-mentioned configuration, it is possible to perform laser treatment by bringing the laser diodes as close as possible to the deepest part of the oral cavity while covering all of the above regions vulnerable to oral mucositis.

Here, the controller 800 may include a microprocessor unit, and unifies and controls the operations of the laser diodes according to instructions programmed in the memory of the microprocessor unit.

The controller 800 operates in any one mode, among a pulse output mode for alternatingly outputting pulses of the first laser diode 822 of 670 nm, the second laser diode 824 of 830 nm, and the third laser diode 826 of 910 nm, a first continuous wave output mode for outputting the first laser diode 822 in the form of a continuous wave, a second continuous wave output mode for outputting the second laser diode 824 in the form of a continuous wave, and a third continuous wave output mode for outputting the third laser diode 826 in the form of a continuous wave according to the input of the mode selection button 120.

The controller 800 may set the pulse width of the second laser diode 824 to be three times longer than that of other laser diodes in the pulse output mode. For example, the controller 800 sets the pulse width of the first laser diode 822 with a wavelength of 670 nm to "250 μs±5%", the off time to "1,350 μs±5%", and the repetition rate to 625 Hz±5%. Then, the controller sets the pulse width of the second laser diode 824 with a wavelength of 830 nm to "950 μs±5%", the off time to "650 μs±5%", and the repetition rate to 625 Hz±5%. Finally, the controller sets the pulse width of the third laser diode 826 with a wavelength of 910 nm to "250 μs±5%" that is the same pulse width as that of the first laser diode 822, the off time to "1,350 μs±5%", and the repetition rate to 625 Hz±5%. A pause of 50 μs is placed between respective wavelengths, and the output operation is performed repeatedly.

When the first laser diode 822 operates in a pulse mode, the 670 nm laser light causes minute bio-damage to the epidermis and dermis. The second laser diode 824 operates in a pulse mode for a longer time than other laser diodes, and the 830 nm wavelength laser penetrates through the dermal layer and deep into the subcutaneous tissue to treat inflammation. Finally, the third laser diode 826 penetrates into the dermal layer, but allows the inflamed region to have a sufficient spontaneous recovery period. By operating the three-wavelength laser in the pulse output mode as described above, the photobiological control mechanism can be sufficiently generated in the oral mucositis region.

Figure 7:
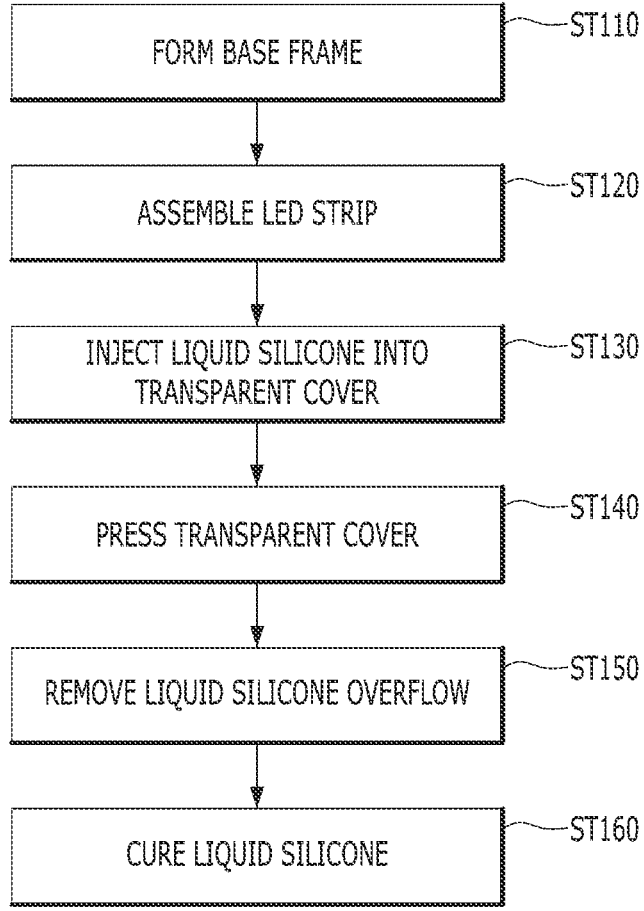
FIG. 7 is a flowchart illustrating a method of manufacturing a laser irradiation device for oral treatment according to the present disclosure.
Figure 8:
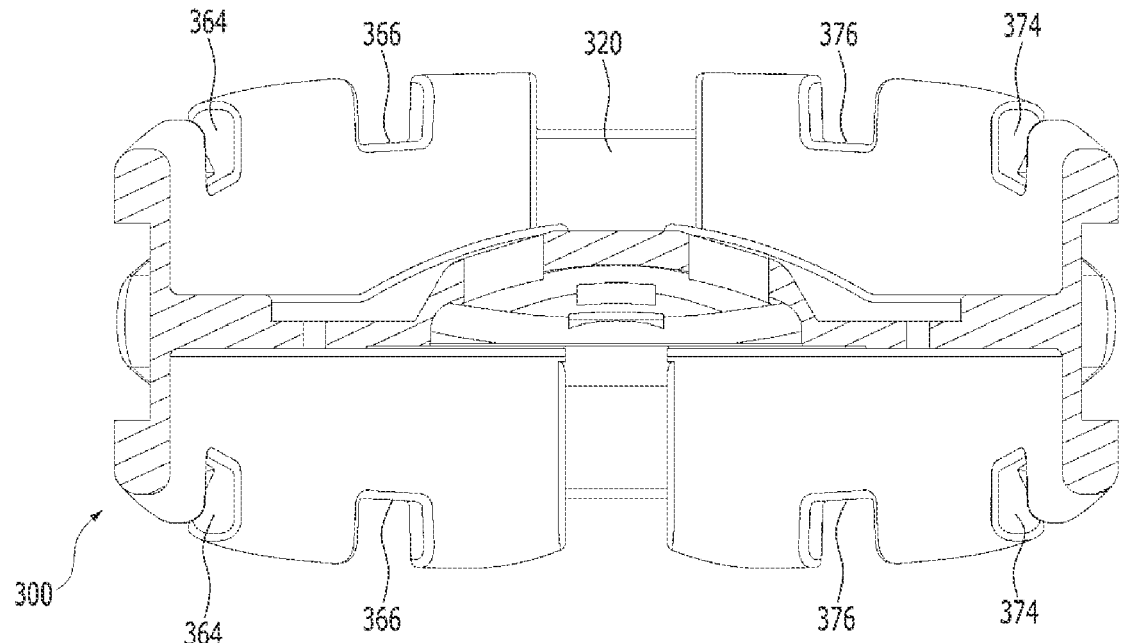
FIGS. 8 to 10 are cross-sectional views illustrating the manufacturing procedure of the laser irradiation device for oral treatment according to the present disclosure.
Figure 9:
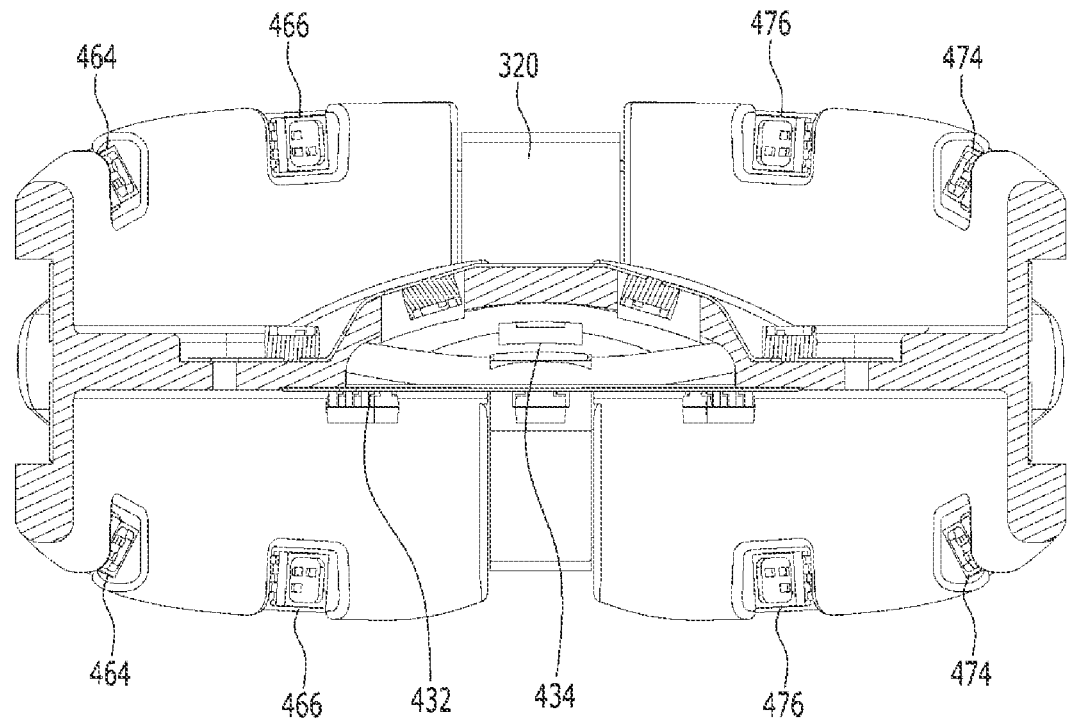
Figure 10:
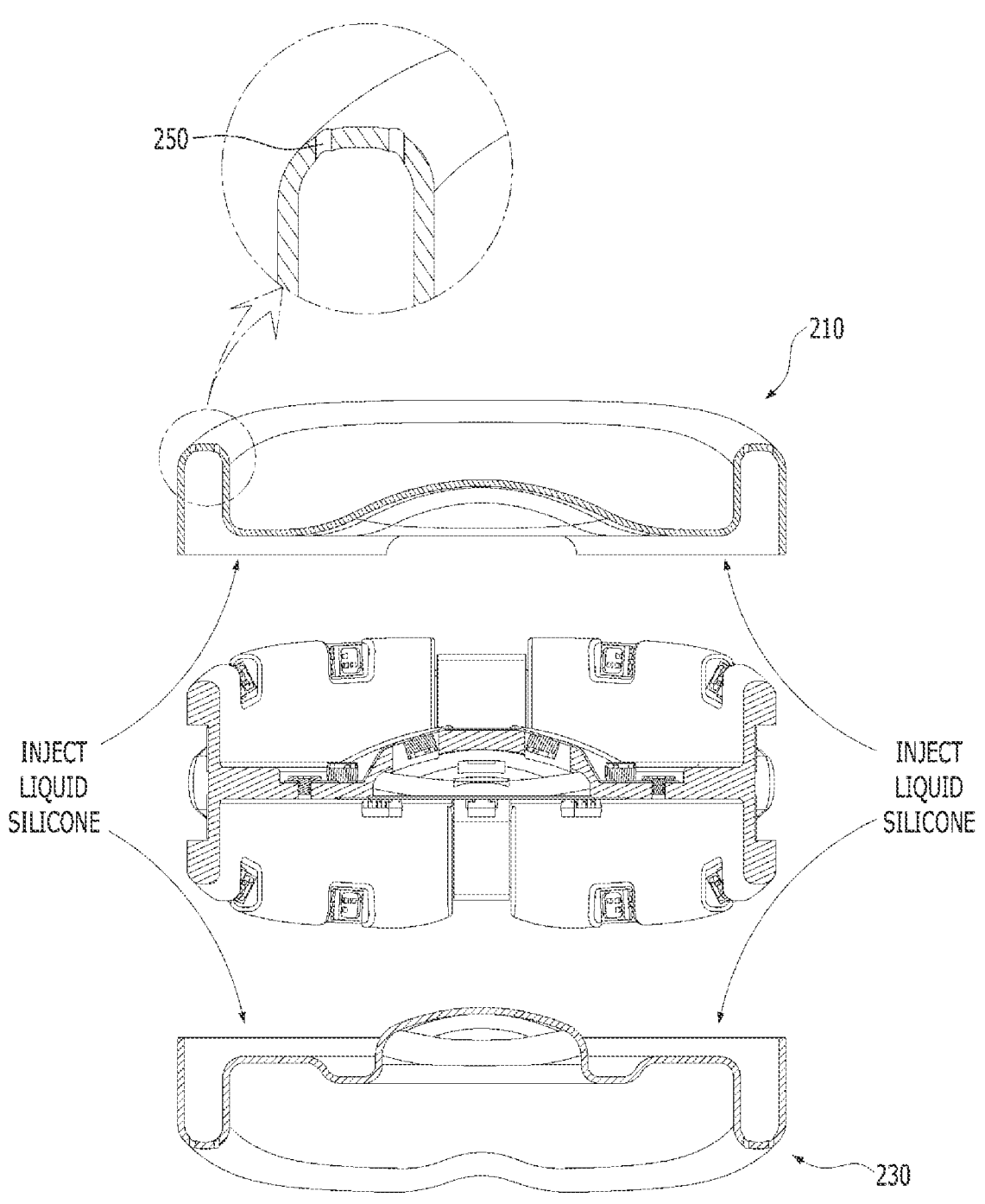

FIG. 7 is a flowchart illustrating a method of manufacturing a laser irradiation device for oral treatment according to the present disclosure, and FIGS. 8 to 10 are cross-sectional views illustrating the manufacturing procedure of the laser irradiation device for oral treatment according to the present disclosure. The method of manufacturing the laser irradiation device for oral treatment according to the present disclosure will be described in detail with reference to FIGS. 7 to 10.

First, as described above, the base frame 300 is molded to have the tongue fixing frame part 330 and the teeth seating part 350 (ST110). The detailed structure of the base frame 300 has been described with reference to FIGS. 1 to 5. The cross-sectional view of FIG. 8 is a cross-sectional view of the base frame 300 cut in the transverse direction, and in FIG. 8, although the first left oral vestibular irradiation seating groove 362 and the first right oral vestibular irradiation seating groove 372 at the edges of the drawing are cut off and not shown, it can be seen that the second left seating groove 364 for oral vestibular irradiation, the third left seating groove 366 for oral vestibular irradiation, the second right seating groove 374 for oral vestibular irradiation, and the third right seating groove 376 for oral vestibular irradiation are located in the vertical direction.

Next, the LED strip 400 illustrated in FIGS. 4 and 5 is assembled onto the base frame 300 (ST120). The cross-sectional view of FIG. 9 shows the state in which the LED strip 400 is assembled with respect to the base frame 300. It can be seen in the drawing that the central laser diode 432 for irradiating the tongue is mounted to face downward, and the laser diode 434 for irradiation of the front side of the palate is mounted to face upward. It can also be seen that the second left oral vestibular irradiation laser diode 464 mounted in the second left oral vestibular irradiation seating groove 364 is provided with a gentler slope than that of the laser diode 466 mounted in the third left oral vestibular irradiation seating groove 366 for the third left oral vestibular irradiation. This will make it possible to irradiate a wide range of laser light closer to the mucositis occurring on the oral vestibule, as the oral vestibule near the canine of the human body has a gentler slope than the oral vestibule near the front teeth.

Next, as illustrated in the cross-sectional view of FIG. 10, a liquid light-transparent resin material (e.g., liquid silicone) is injected into the upper light-transparent cover 210 and the lower light-transparent cover 230 (ST130). The upper light-transparent cover 210 and the lower light-transparent cover 230 may be manufactured by injection-molding of a silicone material to have the shape as described with reference to FIG. 2. At this time, as illustrated in enlarged view of FIG. 10, a plurality of discharge holes 250 is formed in the upper light-transparent cover 210 and the lower light-transparent cover 230 to discharge the liquid silicone to the outside. Preferably, the discharge holes 250 are holes that are sufficiently fine to allow liquid silicone to overflow due to the pressure of the pressing process, and are formed at a position off the optical axis of the laser diode as illustrated in FIG. 10.

Then, the upper light-transparent cover 210 and the lower light-transparent cover 230 are bonded to the base frame 300 by vertically pressing them toward each other (ST140). Next, the liquid silicone overflow escaping to the outside through the discharge holes 250 of the upper light-transparent cover 210 and the lower light-transparent cover 230 during the pressing process is removed (ST150), and the liquid silicone inside the light-transparent covers is cured (ST160). Curing of the liquid silicone may be performed by any one of natural curing using a curing agent, thermal curing, and UV curing.

The embodiment and the accompanying drawings described in the present specification are merely intended to describe a part of the technical spirit included in the present disclosure. Therefore, since the embodiment disclosed in the present specification is not intended to limit the technical spirit of the present disclosure but to explain the technical spirit of the present disclosure, it is obvious that the scope of the technical spirit of the present disclosure is not limited by such an embodiment. Modifications and specific embodiments easily inferred by those skilled in the art within the scope of the technical spirit included in the specification and the drawings of the present disclosure should be construed as being included in the scope of the present disclosure.

What is claimed is:

1. A laser irradiation device for oral treatment, the device comprising:

a base frame having a tongue fixing frame part convexly formed upward so that the tongue is inserted into a lower space thereof, wherein the tongue fixing frame part is provided with a plurality of palate-irradiation seating grooves concavely formed therein, and a teeth seating part concavely formed so that human teeth are seated therein;

an LED strip having a plurality of triple-wavelength laser diodes installed on a flexible circuit board, each triple-wavelength laser diode being configured to be seated in corresponding one of the palate-irradiation seating grooves of the base frame, wherein each triple-wavelength laser diode is in a form of a single chip and includes laser diodes configured to emit three wavelengths of 650-690 nm, 810-850 nm, and 890-930 nm, respectively;

a light-transparent cover coupled to the outside of the base frame and through which laser light emitted from the triple-wavelength laser diodes is transmitted, the light-transparent cover including upper and lower transparent members bonded by pressing a liquid light-transparent silicone resin therebetween, the upper and lower transparent members including a plurality of discharge holes formed at positions off an optical axis of the triple-wavelength laser diodes such that the liquid light-transparent silicone resin is configured to be discharged therethrough thereby eliminating air bubble;

a cable connected to one end of the LED strip to supply operation power to the laser diodes; and a main body including a power supply configured to supply the operation power and a controller configured to control the operation of the laser diodes.

2. The laser irradiation device according to claim 1, wherein the tongue fixing frame part is provided with the plurality of palate-irradiation seating grooves concavely formed such that the triple-wavelength laser diodes mounted on one side of the LED strip are seated therein in a position facing upwards, and a tongue-irradiation cutout such that the triple-wavelength laser diodes mounted on the other side of the LED strip are mounted thereon in a position facing downwards.

3. The laser irradiation device according to claim 1, wherein the base frame is provided such that an end of the tongue fixing frame part is bent at an obtuse angle to form an arc-shaped bent surface for irradiation of the tonsil, and one end of the LED strip is provided with a tonsil division strip branching in an arc shape and on which a plurality of tonsil-irradiation laser diodes is mounted on the bent surface for irradiation of the tonsil.

4. The laser irradiation device according to claim 1, wherein the other end of the LED strip is provided with a sublingual gland division strip branching in a horseshoe shape, and a plurality of sublingual gland-irradiation laser diodes is mounted at predetermined intervals on the sublingual gland division strip, the sublingual gland division strip being mounted on a bottom surface of the base frame.

5. The laser irradiation device according to claim 1, wherein the controller operates in any one mode, among a pulse output mode for alternatingly outputting pulses of a first laser diode, a second laser diode, and a third laser diode, a first continuous wave output mode for outputting the first laser diode in the form of a continuous wave, a second continuous wave output mode for outputting the second laser diode in the form of a continuous wave, and a third continuous wave output mode for outputting the third laser diode in the form of a continuous wave.

6. The laser irradiation device according to claim 5, wherein the controller sets the pulse width of the second laser diode to be three times longer than that of other laser diodes in the pulse output mode.

* * * * *